United States Patent [19]

Boudreau et al.

[11] Patent Number: 5,010,881
[45] Date of Patent: Apr. 30, 1991

[54] ORTHOPEDIC FIXATION DEVICE

[75] Inventors: Michael P. Boudreau; Randall W. Jacoby, both of Greenwood; James L. Laughlin, Hodges, all of S.C.

[73] Assignee: Kirschner Medical Corporation, Timonium, Md.

[21] Appl. No.: 457,082

[22] Filed: Jan. 24, 1990

Related U.S. Application Data

[63] Continuation of Ser. No. 224,826, Jul. 27, 1988.

[51] Int. Cl.$^5$ ............................ A61F 5/01; A61H 1/02
[52] U.S. Cl. ................................. 128/76 R; 128/87 B; 128/89 A
[58] Field of Search ...................... 128/75, 76 R, 87 B, 128/84 R, 89 R, 89 A, 78

[56] References Cited

U.S. PATENT DOCUMENTS 4,541,421 9/1985 Iversen et al. .................. 128/87 B
4,765,317 8/1988 Eastman et al. ...................... 128/75

Primary Examiner—Edgar S. Burr
Assistant Examiner—Stephen R. Funk
Attorney, Agent, or Firm—Frost & Jacobs

[57] ABSTRACT

An improved ambulatory halo device to be worn by a patient for rigid immobilization of the cervical spine has a vest for positionally fixed attachment to the upper torso of the patient, an adjustable framework attached to the vest extending upwardly to adjacent the skull of the patient, and a halo member having a plurality of skull pins adjustably supported on the upper portion of the framework for closely surrounding the skull of the patient. The skull pins are positioned to engage the skull of the patient around the skull above the eyes to rigidly fix the position of the skull and maintain traction on and rigidly fix the position of the cervical spine. The framework is composed of rods and brackets which may be adjustably positioned to positively locate the halo member upon initial attachment to the patient and to permit positional adjustment of the halo member in elevation, anterior/posterior translation and tilt, and rotation about a medial axis of the body of the patient without loss of control of traction on the cervical spine.

7 Claims, 4 Drawing Sheets

ORTHOPEDIC FIXATION DEVICE

This is a continuation, of application Ser. No. 224,826, filed July 27, 1988, now abandoned.

The present invention is directed to an improved orthopedic ambulatory halo device to be worn by a patient for rigid immobilization of the cervical spine.

BACKGROUND OF THE INVENTION

Ambulatory halo devices are employed in the orthopedic field and are applied to be worn by a patient after surgery or an accident to establish traction on and rigidly immobilize the cervical spine. Such devices generally comprise a supporting vest secured in fixed position on the upper torso of the patient, an adjustable framework mounted on the vest, and a halo member, in the form of an open or closed ring, which is mounted on the framework to reside in a position closely surrounding the skull of the patient. The halo member carries a plurality of adjustable skull pins which are positioned in selected openings around the member and are moved radially inwardly to engage and fix the position of the skull relative to the halo and supporting vest. The support framework attaching the halo member to the vest generally includes adjustable rods which extend upwardly from the vest to the head of the patient and additional adjustment means connecting the rods to the halo member so that the halo member can be variably positioned around the skull above the eyebrow line so that the skull pins engage the skull, fix its position, and establish traction on and immobilize the cervical spine of the patient.

To initially apply an ambulatory halo device to a patient after surgery or accident, the patient wearing the vest of the halo device may be placed in a supine position on a support surface, such as an operating table, with the head maintained in desired position by a medical attendant or a suitable head positioning fixture of the table. Generally, the cervical spine is placed under desired traction by application of an external force to the head through a traction bail, and the halo member positioned at the desired location surrounding the skull of the patient. Skull pins are applied to engage the skull at spaced points therearound and the halo member is then fixed in its position by attachment to the framework of the vest.

After application of the halo device to the patient, the patient is usually x-rayed to determine the precise position of the cervical spine and, if not in the position desired, the halo member is repositioned and fixed in new position by precise adjustment of the supporting framework.

Due to the rigidity and strength required in halo devices to ensure positional fixation of the cervical spine, the halo member and its supporting framework which attach it to the vest generally are formed of high-strength materials, such as stainless steel, aluminum, or the like. Metal ambulatory halo devices, because of their electrical conductance, generally are not compatible with computer-tomography, nuclear magnetic resonance, and x-ray investigation of the body of the patient wearer.

U.S. Pat. No. 4,612,930 discloses a head fixation apparatus including crown and skull pins which serves as a halo device for immobilizing the cervical spine in which the crown, or halo, is perferably formed of a boron fiber or graphite fiber-reinforced plastic to avoid blockage during CT scanning, magnetic resonance imaging, and the like.

U.S. Pat. No. 4,541,421 discloses a halo fixation system which is proported to provide for computer tomography (CT), nuclear magnetic resonance (NMR), and x-ray compatibility of the cervical spine and states that the halo and certain of its supporting assemblies can be made of a composite material, such as an acetyl resin, also known as DELRIN. The patent further states that supporting rods of the assemblies can be carbon graphite rods with a fiberglass internal composition, or other suitable materials. The supporting rods of the halo are attached to the vest and elevation assemblies mounted on the rods support the halo. Free-floating ball and socket assemblies adjacent the ends of the rods permit adjustment in elevational tilt and traction of the skull of the patient.

There is also known in the marketplace an ambulatory halo device which appears to be a modification of the halo fixation system described in U.S. Pat. No. 4,541,421, in which the composite material halo member is adjustably attached through opposed support brackets to four positionally adjustable upstanding support rods of the fixation system. The opposed brackets are located adjacent the sides of the head of the wearer and each is mounted for sliding movement along a horizontal slot of a support arm. Each support arm is connected by ball and socket assemblies to be supported on and interconnect the upper ends of a pair of the four upstanding support rods. The brackets may be moved along the slots to correspondingly move the halo in anterior and posterior directions relative to the head of the patient, and arcuate slots provided in the upstanding brackets permit anterior/posterior tilt adjustment of the halo. Vertical slots in the brackets also permit elevational adjustment of the halo relative to the head of the patient.

Ambulatory halo devices manufactured by AOA All Orthopedic Appliances are also known to comprise a molded plastic vest from which a halo is supported adjacent the patient's head by a rigid metal superstructure including a pair of generally inverted metal U-shaped support members attached by an adjustable cross plate to the anterior and posterior portions of the vest. Mounted on the upper curve portions of the inverted U-shaped members just above the shoulder portions of the vest are a pair of upright turn buckles which supportably engage the lateral sides of the halo to provide for its adjustment.

Certain halo devices are also known to be manufactured by Ace Orthopedic wherein the halo member is supported on upstanding rigid support rods mounted on a vest support and provided with means for adjusting the halo member in several directions, including elevation, anterior/posterior translation, and rotation about a medial axis of the patient.

Although ambulatory halo devices of the prior art permit adjustment of the halo member or ring of the device in multiple directions, it is believed that repositioning movement of the halo in certain directions in such devices results in a temporary loss of support of the position of the halo from the vest along a medial line of the patient's body, resulting in corresponding loss of control of traction on the cervical spine of the patient along the medial axis during these repositioning movements. In other words, if it is desired to adjust the position of the halo member in a certain direction with certain of the prior art devices, the upright supporting rods for the halo member must generally be loosened in or from their supports, either at the vest or at their upper ends, as to allow their axial movement relative to the vest or halo and release the traction applied to the cervical spine along the medial axis of the patient's body during the halo repositioning movement.

BRIEF OBJECTS OF THE PRESENT INVENTION

It is an object of the present invention to provide an improved ambulatory halo device for rigid immobilization of the cervical spine having improved means to facilitate precise positional adjustment of the halo member of the device in multiple directions, including elevation, tilt, anterior/posterior translation, and rotation about the medial axis of the body of the patient wearer.

It is a further object of the present invention to provide an improved adjustable ambulatory halo device for rigid immobilization of the cervical spine wherein the halo member may be precisely adjusted in multiple directions and degrees of movement to reposition or adjust the position of cervical spine and skull while maintaining control of traction on the cervical spine along a medial axis of the body of the patient.

SUMMARY OF THE INVENTION

The improved orthopedic ambulatory halo device of the present invention includes a vest to be secured to the upper torso of the patient, an adjustable framework attached to the vest, and a halo member mounted thereon. The framework includes a lower section for gross adjustment of the position of the halo member comprising four generally rigid support rods adjustably attached to and extending upwardly from the vest to reside in respective pairs spaced laterally of the patient's head on opposite sides of the skull, with the upper ends of each pair of rods respectively interconnected by a connector rod which extends alongside the wearer's skull in anterior/posterior direction. The framework further includes an upper section for precise adjustment of the position of the halo member which comprises two adjustment brackets which are attached to a respective connector rod and support the halo member therebetween. Each adjustment bracket is mounted for sliding movement along its connector rod and provides for adjustable positioning of the halo member in elevation along a medial axis of the body of the patient, in rotation about the medial axis, in anterior/posterior tilt and translation, and in lateral tilt while still maintaining control of traction on the cervical spine and vertebra of the patient through the interconnecting framework on the vest during movement of the halo.

The support framework of the halo device permits adjustable positioning of the halo member during initial application of the device on the patient, and permits precise positional readjustment of the skull and cervical spine of the patient after initial attachment of the halo to the skull.

The halo member and supporting framework of the ambulatory halo device may conveniently be formed of high-strength material components, such as metal, or preferably of composite materials which are essentially non-ferrous, non-magnetic, and non-electrically conducting to provide for improved CT, NMR, and x-ray compatibility of the cervical spine and upper body area of the patient.

BRIEF DESCRIPTION OF THE DRAWINGS

The above as well as other objects of the invention will be better understood, and the invention will be better explained by reference to the accompanying drawings, in which.

DETAILED DESCRIPTION OF PREFERRED EMBODIMENTS

Figure 1:
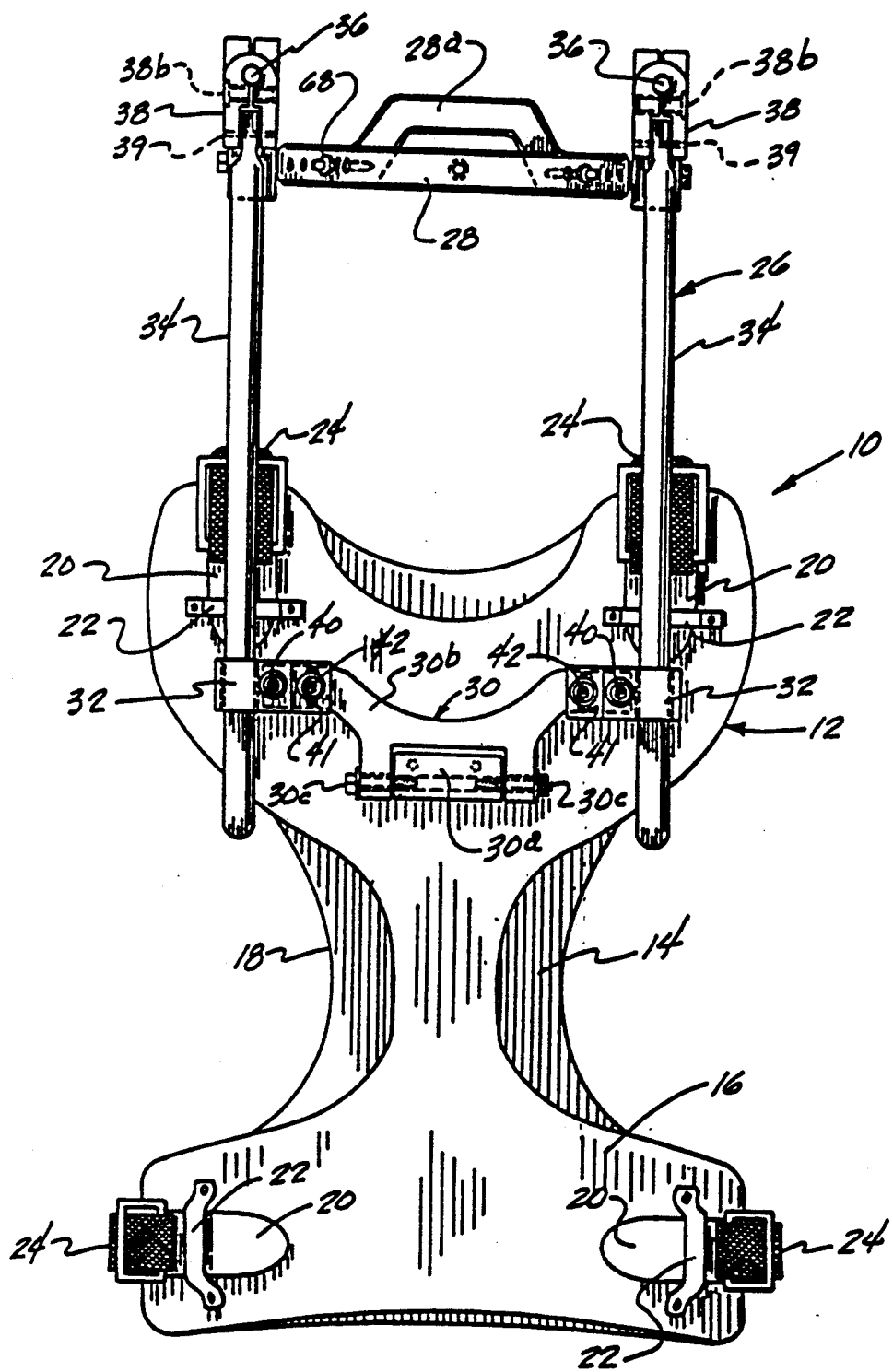
FIG. 1 is a front elevation view of the improved ambulatory halo device of the present invention.

As seen in the drawings, the orthopedic ambulatory halo device 10 of the present invention comprises a supporting vest 12 formed of suitable high-strength, light-weight material, such as molded polyethylene, having a liner 14 of soft padded material, such as natural sheepskin or synthetic polyester fabric material, which may be removably attached thereto by suitable means, such as snaps or VELCRO ® fasteners (not shown). The vest 12 includes anterior and posterior body portions 16, 18 interconnected at their sides at the waist and shoulder areas of a patient by plastic belt-shaped protrusions 20 which are slidably received within channel members 22 on the anterior portion of the vest and are held in position by flexible adjustable straps 24, such as fabric straps with VELCRO ® faces. The size of the vest 12 is determined by the patient's chest circumference and dimensions, and may be suitably cold-formed to accommodate the size of the individual patient. The vest is secured in fixed position on the upper torso of a patient's body when in use.

Figure 2:
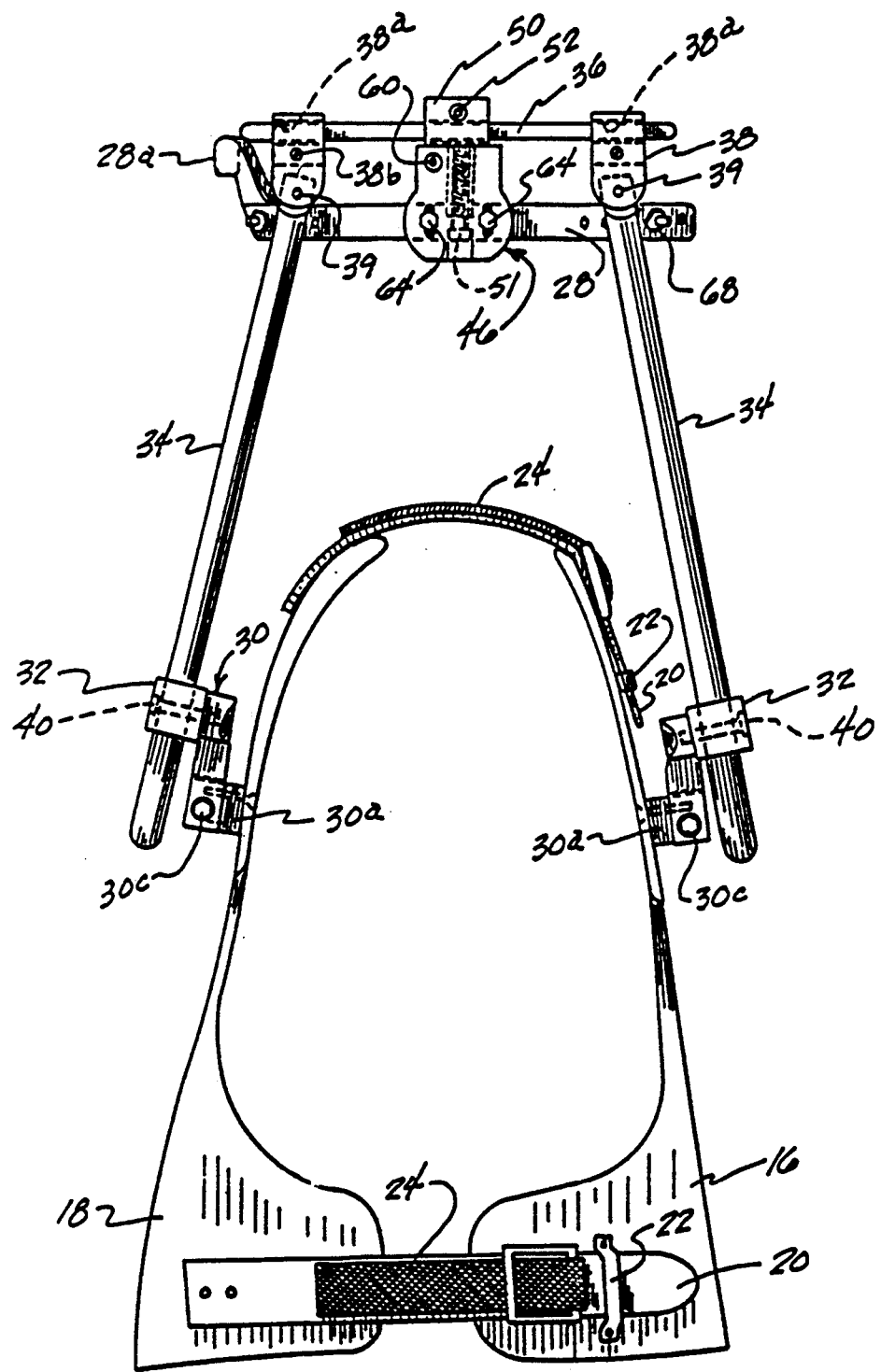
FIG. 2 is a left side elevation view of the halo device of FIG. 1.

Mounted on the vest is a framework 26 for support of a generally oval or racetrack-shaped ring or halo member 28 of the halo device. As seen in FIGS. 1 and 2, framework 26 comprises a lower adjustable section which includes two substantially identical, adjustable yoke-shaped connectors 30 attached respectively to the upper central portion of the anterior and posterior portions of the vest. Each yoke connector 30 includes a support block 30a fixedly attached to the vest, as by rivots, and a yoke section 30b pivotally attached to block 30a by threaded bolts 30c received within internally threaded passageways of the block 30a. The yoke sections 30b may be adjustably pivoted and fixed in their position relative to the block and vest 12 by loosening and tightening bolts 30c.

Figure 5:
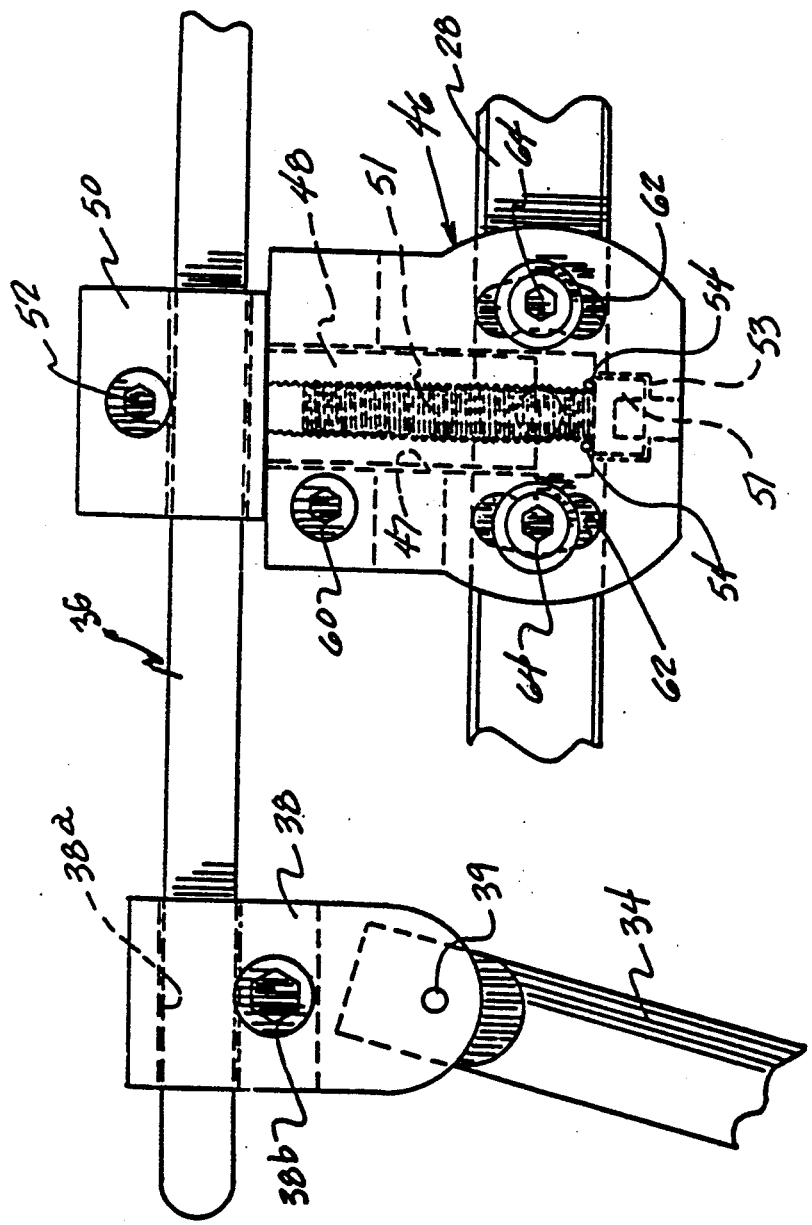
FIG. 5 is an enlarged elevation view of an upper left-hand portion of the framework of the halo device as seen in FIG. 2, showing in greater detail one of the adjustment brackets and the means for attachment of the connector rod with the upper end of one of the upright support rods on the vest.

Mounted on the outer ends of the yoke sections 30b of the connectors 30 on the anterior and posterior portions of the vest 12 by clamp means, shown as friction clamps 32, are four identical upright, rigid support rods (three of which 34 are seen in FIGS. 1 and 2). Attached to the upper end of each rod by a pivot pin 39 are clamp means, shown as a cross clamp 38. As best seen in FIG. 5, each cross clamp 38 is of split construction and surroundingly supports an end of a connector rod 36. The four cross clamps 38 are identical in construction, and each has a central passageway 38a through which the connector rod 36 passes. A fastening bolt 38b connects the split sides of each cross clamp.

As seen in FIGS. 1 and 2, the lower end of each support rod 34 is adjustably attached by a friction clamp 32 to a respective end of the yokes 30b for pivotal adjustment about a pivot bolt 40 and along an arcuate slot 41 by loosening bolt 42, and for upward and downward sliding movement of each rod axially in directions along its longitudinal axis through its clamp by loosening bolt 40.

As best seen in FIGS. 2 and 5, the upper ends of each pair of rods 34 which are located on lateral opposite sides of the head of a patient wearer are pivotally connected to a cross clamp 38 and are interconnected by one of the connector rods 36. The rods 36 are gripped in the cross clamps 38 by the bolt 38b threadably received in each the cross clamp and the bolt may be loosened to permit movement and repositioning of the cross clamps 38 along the connector rods 36, and to permit pivotal, angular adjustment of the support rods 34.

Mounted for movement along each connector rod 36 between the cross clamp 38 thereon is an adjustment bracket 46 for supporting and adjustably positioning the halo member 28. The adjustment brackets 46 are of substantially identical construction and, as best seen in FIG. 5 which is an enlarged side elevation view of a left-hand portion of the support framework and halo member as seen in FIG. 2, each bracket 46 includes a housing having an upper cylindrical opening with passageway 47 extending downwardly thereinto. Passageway 47 receives for sliding movement therein the end of a cylindrical post 48 of a clamp means, shown as a split traverse sleeve 50. Each traverse sleeve 50 has a central passageway and is received for sliding movement on a respective connector rod 36. A threaded member or locking bolt 52 extending through and threadably received in one of the split sides of each traverse sleeve 50 may be loosened to permit sliding adjustable movement of the sleeve 50 and bracket 46 along the length of its connector rod 36 to provide correspondingly adjustable movement of the halo member 28 anteriorly and posteriorly relative to the head of the patient wearer.

The cylindrical post 48 of each traverse sleeve 50 is internally centrally threaded to receive an elevator bolt 51, the head of which is retained in the lower portion of the central passageway 47 by abutment with a lower internal radial shoulder 53 of the passageway and a pair of set pins 54 in the housing of bracket 46 which engage the head of bolt 51. The outer wall of each adjustment bracket 46 is provided with a pivot pin 61 (FIGS. 3 and 5) which is received within a recess in a side wall of the halo member 28. The elevator bolt of each bracket may be rotated by a suitable tool inserted into the bracket housing through a lower access passageway 56 to raise or lower the housing of adjustment bracket 46 on the post 48 of the traverse sleeve 50, thus providing for elevational adjustment of the halo member 28 along a medial axis relative to the skull of the patient. As best seen in FIG. 5, the housing of each adjustment bracket 46 is split on one side thereof and a fastening bolt 60 is employed to move the split portion of the housing into and out of engagement with the upright post 48 of the traverse sleeve 50 to frictionally fix the position of the adjustment bracket 46 on the post.

Each bracket 46 has a pair of radially disposed arcuate slots 62 which receive a pair of locking means, shown as bolts 64, the inner ends of which are received in internally threaded openings in the halo member. By loosening locking bolts 64, the halo member 28 may be pivoted about the pivot pins 61 to provide anterior/posterior tilt adjustment of the halo member relative to the patient.

Figure 3:
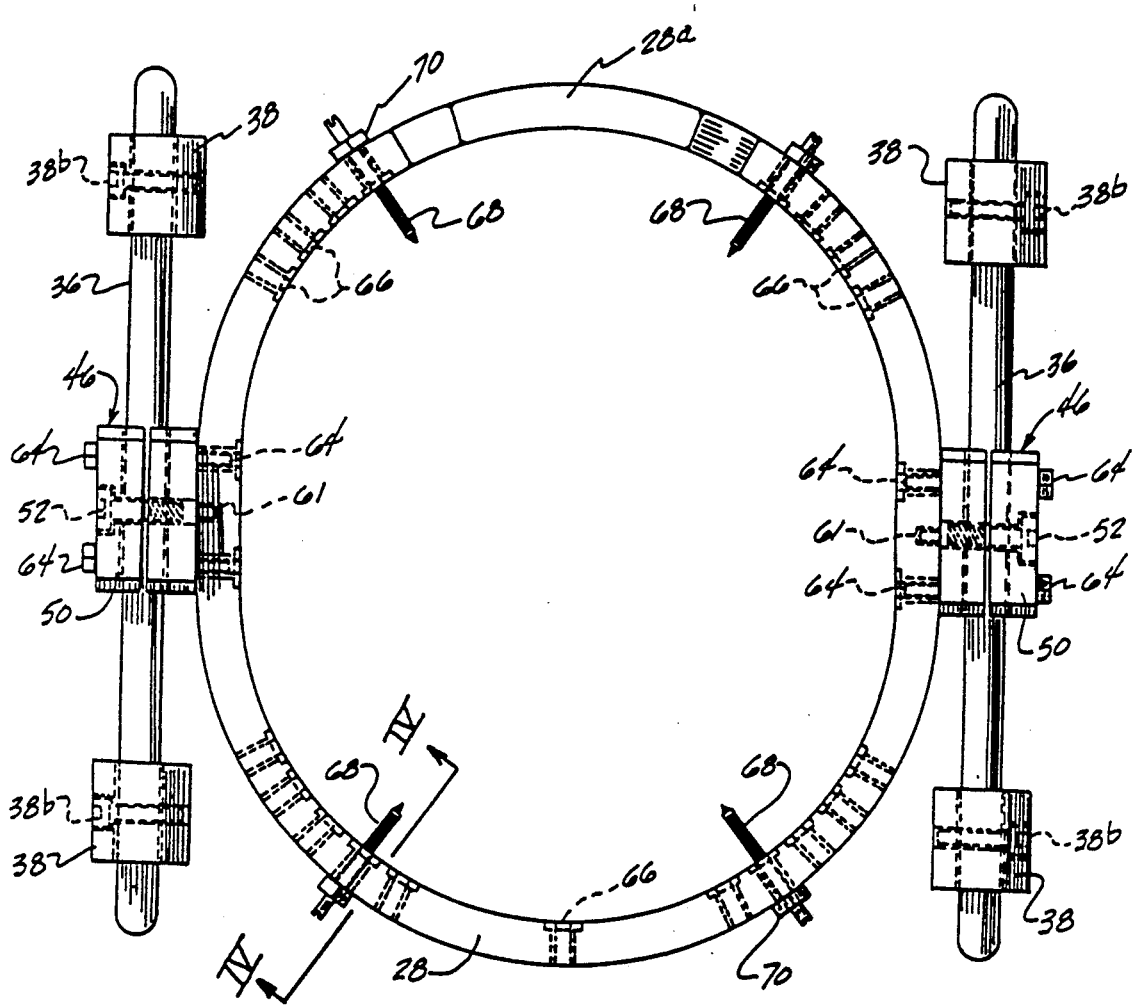
FIG. 3 is an enlarged top plan view showing only the halo member and an upper portion of the support framework of the halo device of FIGS. 1 and 2.
Figure 4:
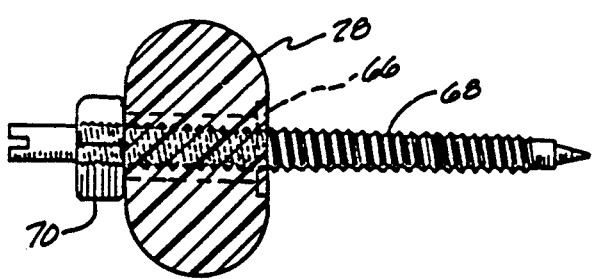
FIG. 4 is a cross-sectional elevation view of the halo device taken along line IV—IV of FIG. 3, looking in the direction of the arrows.

As seen in FIGS. 1-3, halo member 28 is shown as a closed ring of generally racetrack shape having a higher cervical arch portion 28a located posterior, or to the rear, of the skull of the patient to provide access to the cervical spine for operative procedure thereon, if desired. The halo member 28 is provided with a number of arcuately disposed holes therethrough, with internally threaded sleeves 66 disposed or formed therein A plurality of threaded skull pins 68 with locking nuts 70 may be selectively positioned in the sleeves 66 and rotatably adjusted to engage the skull of the patient at arcuately spaced locations around the skull of the patient generally just above the eye level to fix the position of the skull in the halo member. Although the halo member 28 is shown in the drawings as being support and disposed by the adjustable brackets 46 in a plane below connector rods 36, as seen in FIGS. 1, 2, and 5, the halo member could be supported and disposed in a plane above the connector rods 36 by inverting the position of the brackets on the rods 36.

From the foregoing description of preferred embodiments of the present invention, it can be seen that the ambulatory halo device, as described, provides for rigid immobilization of the cervical spine of the patient wearer, and permits adjustment of the halo member of the device both at the time of initial application of the device to the patient wearer and after application, in multiple directions of adjustment. For gross positional adjustment of the halo member, the supporting rods 34 of the framework may be elevated and/or angularly positioned relative to the vest at the time of initial installation of the device on a patient. For example, by loosening bolts 40 of friction clamps 32 on connector yokes 30, rods 34 may be slid in their clamps 32 axially along their lengths to raise or lower the halo member relative to the medial axis of the patient. By also loosening bolts 42 and bolts 38b, the halo member may be shifted in lateral translation relative to the patient through a distance determined by the length of slots 41. By loosening bolts 30c on the connector yokes 30 and bolts 8b on cross clamps 38, the halo member may be shifted in anterior/posterior translation relative to the patient.

The position of the halo member also may be precisely and finely adjusted within narrower limits in multiple directions and degrees of movement after attachment to the patient and while maintaining control of traction on the cervical spine of the patient. As can be appreciated, traction is maintained on the cervical spine by controlling the distance in elevation of the halo member 28 from the vest 12 along a medial axis of the body of the patient. Thus, by restraining support rods 34 from axial movement in their friction clamps 32 during adjustment and repositioning of the halo member, the position of the skull of the patient can be supported by the vest at a given distance above the patient's shoulders. To illustrate, with the skull pins of the halo member engaged with the skull of the patient in fixed position relative thereto, and after release of locking bolts 60 to permit rotation of the housings of the adjustment brackets 46 about support posts 48, the traverse sleeves 50 of the adjustment brackets may be moved in opposite directions along their respective connector rods 36 on opposite sides of the head of the patient to rotatably adjust position of the halo member about a medial axis of the patient's body. To permit this rotational adjustment, the four support rods 34 have sufficient inward flexure, as seen in FIG. 1, to allow up to about twenty degrees of rotation of the halo member, without necessity of release of the lower ends of the rods from their friction clamps 32, thus retaining control of traction of the cervical spine.

Likewise, loosening of bolts 64 provides for anterior/posterior tilt adjustment of the halo member, while rotation of the elevator bolts 52 of the adjustment brackets provides for elevational adjustment along the medial axis of the patient without loss of control of traction on the cervical spine.

The halo member may be adjusted precisely in lateral tilt by loosening bolt 52 on traverse sleeve 50 on one side of the halo member while rotating the elevator bolt 52 in bracket 46 on the other side of the halo member. The supporting rods 34 may be precisely positioned along the lengths of the connector rods by loosening bolts 38b of the split cross clamps 38 and the corresponding threaded bolts 30c of the yoke connectors 30 mounted on the vest. This adjustment permits the relative distance between the cross clamps on either of the connector rods 36 to be varied along the rods, an adjustment which may be desired when operative procedures are to be carried out on the neck or head of the patient.

The halo member may be adjusted in anterior/posterior translation by loosening bolts 52 of the traverse sleeves 50 to slide the traverse sleeves 50 simultaneous in the same direction along their connector rods 36. Anterior/posterior translation of the halo member may also be accomplished by loosening bolts 30c of the anterior and posterior yoke connectors 30 and bolts 38b of cross clamps 38 to allow pivotal movement of support rods 34 and shifting of the rods 36 forwardly or rearwardly relative to the patient's head.

It can thus be seen that the halo member may be precisely adjusted in elevation, rotation about a medial axis of the patient's body, in anterior/posterior tilt and translation, and lateral tilt, all while maintaining control of traction on the cervical vertebrae through the upright support rods 34 which retain their fixed position relative to the medial axis of the body of the patient wearer.

As hereinbefore mentioned, all component parts of the ambulatory halo device of the present invention may be formed of essentially non-ferrous, non-magnetic, and non-electrically conductive materials, such as a plastic or fiber-reinforced plastic composite material. The halo member 28, the housings of the adjustment brackets 46, sleeves 38, connector rods 36, cross clamps 38, and the upright support rods 34 of the device may be formed of a suitable composite material, such as a fiber-reinforced polycarbonate or epoxy resin, while the skull pins 68 and all fastening bolts of the support structure of the halo device may be formed of titanium. As mentioned the vest may be formed of a suitable plastic, such as polyethylene, and the support structure 26 attached thereto by plastic rivots or the like. In this manner, the entire halo device offers essentially no interference with CT, NMR, and x-ray investigation of the cervical spine and upper body area of the patient.

That which is claimed is:

1. An improved ambulatory halo device to be worn by a patient for rigid immbilization of the cervical spine comprising vest means for positionally fixed attachment to the upper torso of the patient, a halo member for closely surrounding the skull of a patient between the eyes and the top of the skull, said halo member having a plurality of radially adjustable skull pins disposed about the halo for engagement with the skull of the patient to fix the position of the skull relative to the halo member, and framework means for adjustably fixing the position of the halo member relative to the vest means to maintain traction on and rigidly immobilize the cervical spine of the patient; said framework means comprising first and second pairs of generally rigid support rods having upper and lower end portions, means attaching said lower end portion of each support rod to the vest, means for adjustable axial movement of each support rod and for adjustable pivotal movement in an anterior/posterior direction and a lateral direction whereby said upper end portions of said first pair of said support rods may be generally positioned in anterior/posterior spaced relation laterally on one side of the skull of a patient and said upper end portions of said second pair of said support rods may be generally positioned in anterior/posterior spaced relation laterally on the other side of the skull, means interconnecting said upper end portions of said support rods of each pair on each side of the skull comprising a first clamp means pivotally attached to said upper end portion of each support rod, a rigid connector rod extending between said support rods of each respective pair and grippingly held within said first clamp means on said support rods whereby a connector rod extends in anterior/posterior direction on each side of the skull of the patient, and an adjustable bracket means mounted for sliding movement along and for fixed location on each connector rod, each bracket means including means engaging an opposite side portion of the halo member for positional adjustment of the halo member in elevation, anterior/posterior translation and tilt, and in rotation about a medial axis of the body of a patient without loss of control of traction on the cervical spine of the patient, each of said adjustable bracket means comprising a housing having means for pivotal attachment of said halo member thereto for said anterior/posterior tilt adjustment of the halo relative to the patient, each housing including a central passageway therein, each of said adjustable bracket means further comprising a second clamp means attached to its respective connector rod and having a post slidably received within the housing passageway, and means for adjustably positioning the housing along the longitudinal axis of the post to positionally adjust the halo member in elevation relative to the patient.

2. A halo device as defined in claim 1 wherein said adjustable bracket means includes means for positional adjustment of the halo member in lateral tilt without loss of control of traction on the cervical spine of the patient.

3. A halo device as defined in claim 1 wherein said means for each bracket means housing along the longitudinal axis of the post comprises a threaded member mounted axially in said housing passageway for rotational movement about its axis and fixed against relative movement along said passageway, a threaded recess in said post, and said threaded member being threadably received within said threaded recess whereby rotation of the threaded member causes sliding movement of said post in said housing passageway and elevational adjustment of said halo member.

4. A halo device as defined in claim 1 wherein each of said first clamp means has a passageway therethrough and surrounds its respective connector rod, and releasable locking means for grippingly securing each of said first clamp means in a fixed position on its connector rod and for releasing each first clamp means to permit its sliding movement along the connector rod and to permit pivotal movement of the support rod attached thereto about its point of attachment.

5. A halo device as defined in claim 1 wherein each adjustable bracket means for positional adjustment of the halo member in anterior/posterior tilt includes a pivot pin extending outwardly from said housing and received within a recess in said halo member, arcuate slot means through said housing disposed radially of said pivot pin, and locking means extending through said arcuate slot means and received within a recess in said halo member, and said locking means being adjustable to permit pivotal movement of the housing about the pivot pin along the arcuate slot means and for fixing the position of the halo member at a desired degree of tilt within the limits of the slot means.

6. A halo device as defined in claim 1 wherein said means adjustably attaching said lower end portion of each support rod to the vest means comprises two yoke-shaped connector means each respectively pivotally attached to an anterior and posterior portion of the vest means for pivotal movement of said yoke-shaped connectors about a lateral axis relative to the patient, a third clamp means mounted on the end portions of each of the yoke-shaped connector means, each third clamp means having a passageway therethrough and grippingly engages a respective one of said rigid support rods to permit its axial adjustment along its longitudinal axis to provide for elevational positional adjustment of the halo member, and each of said third clamp means including means providing limited pivotal movement of each support rod generally about an anterior/posterior axis relative to the patient.

7. An improved ambulatory halo device to be worn by a patient for rigid immobilization of the cervical spine comprising vest means for positionally fixed attachment to the upper torso of the patient, a halo member for closely surrounding the skull of a patient between the eyes and the top of the skull, said halo member having a plurality of radially adjustable skull pins disposed about the halo for engagement with the skull of the patient to fix the position of the skull relative to the halo member, and framework means for adjustably fixing the position of the halo member relative to the vest means to maintain traction on and rigidly immobilize the cervical spine of the patient; said framework means comprising first and second pairs of generally rigid support rods having upper and lower end portions, means attaching said lower end portion of each support rod to the vest, means for adjustable axial movement of each support rod and for adjustable pivotal movement in an anterior/posterior direction and a lateral direction whereby upper end portions of a first pair of said support rods may be generally positioned in anterior/posterior spaced relation laterally on one side of the skull of a patient and upper end portions of a second pair of said support rods may be generally positioned in anterior/posterior spaced relation laterally on the other side of the skull, means interconnecting said upper end portions of said support rods of each pair on each side of the skull comprising a first clamp means pivotally attached to the upper end of each support rod, a rigid connector rod extending between the support rods of each respective pair and grippingly held within said first clamp means on the support rods whereby a connector rod extends in anterior/posterior direction on each side of the skull of the patient, and an adjustable bracket means having second clamp means mounted for sliding movement along and for fixed location on each connector rod, each bracket means including means engaging an opposite side portion of the halo member for positional adjustment of the halo member in elevation, anterior/posterior translation and tilt, and in rotation about a medial axis of the body of a patient without loss of control of traction on the cervical spine of the patient, said means adjustably attaching said lower end portion of each support rod to the vest means comprising two yoke-shaped connector means each respectively pivotally attached to an anterior and posterior portion of the vest means for pivotal movement of said yoke-shaped connectors about a lateral axis relative to the patient, a third clamp means mounted on the end portions of each of the yoke-shaped connector means, each third clamp means having a passageway therethrough and grippingly engages a respective one of said rigid support rods to permit its axial adjustment along its longitudinal axis to provide for elevational positional adjustment of the halo member, and each of said third clamp means including means providing limited pivotal movement of each support rod generally about an anterior/posterior axis relative to the patient.

* * * * *

UNITED STATES PATENT AND TRADEMARK OFFICE
CERTIFICATE OF CORRECTION

PATENT NO. : 5,010,881

DATED : April 30, 1991

INVENTOR(S) : Michael P. Boudreau, Randall W. Jacoby and James L. Laughlin

It is certified that error appears in the above-identified patent and that said Letters Patent is hereby corrected as shown below:

Claim 1 - Line 2 - Column 8 - the word "immbilization" should be deleted and replaced with -- immobilization --

Claim 3 - Line 61 - Column 8 - the word -- moving -- should be inserted before "each bracket means"

Signed and Sealed this

Twenty-ninth Day of September, 1992

Attest:

DOUGLAS B. COMER

Attesting Officer

Acting Commissioner of Patents and Trademarks